United States Patent [19]

Sanders et al.

[11] Patent Number: 4,722,890
[45] Date of Patent: Feb. 2, 1988

[54] QUANTITATIVE ASSAY FOR HUMAN TERMINAL COMPLEMENT CASCADE ACTIVATION

[75] Inventors: Martin E. Sanders, Gaithersburg; Keith A. Joiner, Rockville; Michael M. Frank, Bethesda; Carl H. Hammer, Gaithersburg, all of Md.

[73] Assignee: The United States of America as represented by the Department of Health and Human Services, Washington, D.C.

[21] Appl. No.: 769,684

[22] Filed: Aug. 27, 1985

[51] Int. Cl.$^4$ .............................................. G01N 53/00
[52] U.S. Cl. ......................................... 435/7; 436/821
[58] Field of Search ..................... 435/7, 536; 436/821

[56] References Cited

PUBLICATIONS

Weeks et al.—Chem. Abst. vol. 103 (1985) p. 86098t.
Morgan et al.—Chem. Abst. vol. 99 (1983) p. 210,882j.
Bhakdi et al. (1983) Journ. of Immun. Meth. 57:283–289.
Falk et al. (1985) N. Engl. Journ. Med. 312:1594–1599.
Mollnes et al. (1984) Scand. J. Immunol. 20:157–166.
Podack et al. (1984) Molecular Immun. 21:589–603.
Sanders et al. (Abstract) *Cellular Interactions of Complement II.*
Fed. Proc. 44 (1985) and *Clinical Research* 33 (1985).

*Primary Examiner*—Sam Rosen
*Attorney, Agent, or Firm*—Holman & Stern

[57] ABSTRACT

The present invention discloses an enzyme-linked immunosorbent assay (ELISA) to quantitate fluid phase terminal complement activation. Upon activation to form C5b-9, terminal complement components express neoantigens not present in the unassembled individual components. Rabbit antiserum to polymerized C9 was rendered specific for C9 neoantigenic determinants by serial immunosorbtion with human serum, human C9, and other terminal complement components bound to Sepharose. Using the IgG from this antiserum, a sandwich ELISA was devised to bind SC5b-9 from solution onto polystyrene plates. The ELISA plates were developed with the use of goat antiserum to native C9 epitopes followed by a swine anti-goat IgG alkaline phosphatase conjugate. Quantitation of SC5b-9 in solution was performed by comparing sample OD to a standard curve generated with human SC5b-9 that was purified from zymosan-activated serum. The assay is sensitive to as little as 100 ng of SC5b-9/ml and is useful for screening plasma, serum, cerebrospinal fluid, or other biological fluids for the presence of terminal complement cascade activation.

6 Claims, 7 Drawing Figures

QUANTITATIVE ASSAY FOR HUMAN TERMINAL COMPLEMENT CASCADE ACTIVATION

BACKGROUND OF THE INVENTION

1. Technical Field

The present invention is related to a method of quantitation of activation of the human terminal complement cascade. More particularly, the present invention is related to a kit and a quantitative method for fluid phase human terminal complement cascade activation by enzyme-linked immunosorbent assay.

2. State of the Art

It has been reported that the terminal complement cascade is activated in a variety of human diseases, including the glomerulonephritis and cutaneous lesions of systemic lupus erythematosus (Biesecker et al. *J. Exp. Med.* 154: 1779, 1981; Biesecker et al., *N. Engl. J. Med.* 306: 264, 1982; Falk et al. *Clin. Research* 32:503A (Abstract), 1984), other glomerulonephritides (Falk et al. *J. Clin. Invest.* 72:560, 1983), bullous pemphigoid (Dahl et al. *J. Invest. Dermatol.* 82:132, 1984), dermatitis herpetiformis (Dahl et al. *Arch. Dermatol.* 121:70, 1985), and demyelinating diseases (Sanders et al. *Clin. Research* 33:388A (abstract), 1985). However, a quantitative and sensitive enzyme linked immunosorbent assay to determine or detect the activation of the terminal cascade in the human body fluid is not available. Therefore, the availability of a simple, sensitive assay which measures activation of the terminal complement components should prove useful for studying the pathophysiology of a variety of disease states and for monitoring disease activity.

Activation of the terminal portion of the complement cascade results in the assembly of a macromolecular complex consisting of C5b, C6, C7, C8 and a variable number of C9 monomers. If activation occurs in the fluid phase, two or three molecules of S protein combine with the complex, making it cytolytically inactive (Kolb and Muller-Eberhard *Proc. Natl. Acad. Sci. U.S.A.* 72:1687, 1975). However, this SC5b-9 complex is water soluble and contains 2-3 C9 monomers. In the presence of a target membrane, the activation of the terminal complement cascade results in the formation of the MC5b-9 complex, which is cytolytically active (Mayer *Proc. Natl. Acad. Sci.* 69:2954, 1972). The MC5b-9 complex contains a variable number of C9 monomers, as many as 12 to 16, depending on the availability of C9 (Podack et al. *J. Exp. Med.* 156:268, 1982; Bhakdi and Tranum-Jensen *J. Immunol.* 133:1453, 1984). Furthermore, purified human C9 alone if incubated at 37° C. spontaneously forms closed-ring, SDS-resistant polymerized C9 (poly C9) (Podack and Tschopp *Proc. Natl. Acad. Sci. U.S.A.* 79:574, 1982) and polymerization of purified C9 results in expression of a C9 neoantigen. This C9 neoantigen- is also expressed in SC5b-9 and MC5b-9 complexes (Podack and Tschopp *J. Biol. Chem.* 257:15204, 1982; Falk et al. *J. Clin Invest.* 72:560, 1983), as are several other neoantigens related to other steps in C5b-9 assembly (Kolb and Muller-Eberhard *J. Exp. Med.* 141:734, 1975).

Polyclonal antibodies directed to all of the neoantigens of SC5b-9 have been used in an immunoradiometric assay for SC5b-9 (Bhakdi and Muhly *J. Immunol. Methods* 57:283, 1983). This assay, which is based on the inhibition of binding of radiolabeled antineoantigen antibodies to rabbit erythrocyte membranes bearing MC5b-9 lesions, is sensitive to 3 to 4 μg of SC5b-9 per ml, equivalent to a 1% activation of the terminal complement components in normal serum. In another competitive inhibition radioimmunoassay for SC5b-9 (Falk et al. *Clin. Research* 32:503A (abstract), 1984), a monoclonal antibody to the C9 neoantigen was used. In this assay, radiolabeled polymerized C9 was displaced from the monoclonal antibody by the SC5b-9 present in the test sample. A standard curve was created using unlabeled poly C9, and the results were expressed as unit equivalents of poly C9 rather than as units of SC5b-9. The sensitivity of the assay was not reported. Finally, an enzyme-linked immunosorbent assay (ELISA) for SC5b-9 has been described which, in a sandwich fashion, uses antibodies to native epitopes in two different complement components present in the assembled C5b-9 complex. Although this approach yields a sensitive assay for SC5b-9, the utility of the assay is limited in that its signal can be inhibited by normal human serum (Mollnes et al. *Scand. J. Immunol.* 20:157, 1984).

The present invention discloses a method which does not have the limitations or disadvantages of the prior art assays. Definitions of certain terms used herein may be found in Podack et al, *Mol. Immunol.* 21:589–603, 1984 which is incorporated herein by reference.

SUMMARY OF THE INVENTION

It is, therefore, an object of the present invention to provide a simple, sensitive and quantitative assay to detect the activation of terminal complement cascade.

It is a further object of the present invention to provide an enzyme-linked immunosorbent assay (ELISA) for quantitative determination of terminal complement cascade activation using the human body fluid.

It is a still further object of the present invention to provide an ELISA for C9 neoantigen which allows quantitation of about 100 ng or less of SC5b-9 per ml of the body fluid.

An additional object of the present invention is to provide a kit comprising containers containing necessary components of the ELISA of the present invention.

Other objects and advantages of the present invention will become evident as the detailed description of the present invention proceeds.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 3 shows double diffusion in 1% agarose. Center well contained unabsorbed anti-C9 neoantigen. Precipitin lines are seen with poly C9 at 12 and 6 o'clock and with MC5b-9 at 10 o'clock. Lines of partial identify are seen with native C9 and 2 and 8 o'clock. No lines were detected against normal plasma at 4 o'clock;

DETAILED DESCRIPTION OF THE INVENTION

Figure 1:
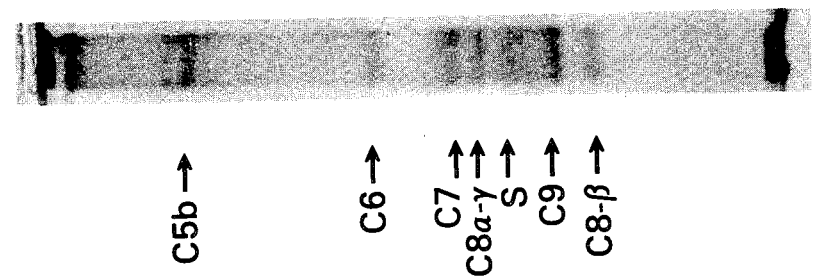
FIG. 1 shows Coomassie-stained SDS-PAGE of SC5b-9, 6.5% acrylamide, non-reduced. There were bands of appropriate $M_r$ to represent C5, C6, C7, C8α-γ, C8β, C9 and S protein. Minimal contamination with other proteins was detected. The presence of C5, C6, C7, C8, and C9 was shown in this material by double diffusion and immunoelectrophoresis.

The above objects and advantages of the present invention are achieved by a method for assaying activation of terminal complement cascade, comprising in sequence the steps of:

(a) coating a suitable surface with a sufficient amount of a first antibody having specificity for poly C9 antigen;

(b) washing said surface with a suitable medium to remove unbound antibody;

(c) incubating said surface with a sample to be assayed for sufficient time so that binding reaction between said sample and the first antibody is substantially complete;

(d) washing said surface with a suitable medium to remove unbound sample;

(e) incubating said surface with a second antibody specific for a constituent of the terminal cascade for sufficient time so that binding between antigen and the second antibody is substantially complete;

(f) thereafter washing the surface with a suitable medium to remove unbound second antibody;

(g) incubating said surface with a third antibody which recognizes the second antibody and which is conjugated with a suitable enzyme for a sufficient time so that the binding between said second and third antibodies is substantially complete;

(h) washing said surface with a suitable medium to remove unbound third antibody;

(i) incubating the surface with a substrate specific for the conjugated enzyme for sufficient time so that the enzyme-substrate reaction is substantially complete; and (j) measuring the product resulting from enzyme-substrate reaction relative to known amounts of SC5b-9 standard similarly treated as in steps (a) thru (j).

The term "substantially complete" as used herein means that the reaction is as complete as can be expected under the test conditions.

The term "body fluid" as used herein means blood, plasma, serum, cerebrospinal fluid, urine and the like.

Although any similar or equivalent materials and methods can be employed for the practice of the present invention, the following are the preferred methods and materials. All publications cited hereunder are incorporated herein by reference.

Buffers

The following buffers were used: isotonic Veronal-buffered saline prepared with 0.1% gelatin, 0.15 mM $CaCl_2$, 1 mM $MgCl_2$, 0.15M NaCl, 1 g/l diethyl barbiturate, pH 7.35 (GVBS++); lysine-Sepharose buffer containing 0.15M NaCl, 0.01M ethylenediaminetetraacetic acid (EDTA), and 0.05M $K_2HPO_4$, pH 7.3; and PBS-Tween containing 0.15M NaCl, 10 mM $PC_4$, and 0.05% Tween 20 (Fisher Scientific, Fair Lawn, NJ), pH 7.2.

Purified complement components

Partially purified C5, C6, C7, and C8 in addition to highly purified C9 were isolated in accordance with the methods of Hammer et al. *J. Biol. Chem.* 256:3995, 1981. Prior to use, C9 was further purified by elution from a hydroxylapatite column with a phosphate buffer gradient as described by Biesecker and Muller-Eberhard, *J. Immunol.* 124:1291, 1980. [$^{125}$I]Na (Amersham, Arlington Heights, IL) was used to radiolabel the C9 with the use of iodobeads (Pierce Chemical Co., Rockford, IL).

Polymerization of C9

Poly C9 was isolated by modification of the previously published method of Podack and Tschopp, *J. Biol. Chem.* 257:15204 (1982). Five milligrams of purified C9 at 2 mg/ml, with a trace of $^{125}$I-C9 added, was incubated at 37° C. for 63 hr in 10 mM Tris, 15 mM NaCl buffer containing 0.02% sodium azide, 25 μM p-nitrophenyl-p-guanidinobenzoate HCl, and 50 μg/ml of soybean trypsin inhibitor. The product was chromatographed on a Biogel A5M (Biorad, Richmond, VA) column (90×1.5 cm), and the $^{125}$I-C9-containing peak eluting just behind the void volume was pooled. Electrophoresis in a 2.5 to 10% SDS-PAGE slab gel revealed the presence of SDS non-dissociable poly C9 migrating as a broad band in the 2.5% portion of the gel (Podack and Tschopp *Proc. Natl. Acad. Sci.* USA 79:574, 1982).

Purification of SC5b-9

SC5b-9 was isolated by the method of Ware et al. *Molec. Immunol.* 18:521 (1981) modified as follows. One hundred milliliters of fresh human serum containing a trace amount of $^{125}$I-C9 was activated with zymosan, at 15 mg/ml, for 2 hr at 37° C. The zymosan was removed by centrifugation, and polyethylene glycol, 8% wt/vol, was added to the supernatant. The mixture was stirred at 4° C. for 30 min. The resulting precipitate was collected, resuspended in lysine Sepharose buffer, and applied to an anti-C5 immunosorbent column with a bed volume of 40 ml. The column was washed with 4 volumes of lysine Sepharose buffer and then eluted with 4M guanidine HCl. The eluted protein was dialyzed against lysine Sepharose buffer, concentrated, and applied to a Sepharose 6B-Cl column with a bed volume of 500 ml. Two protein peaks eluting just behind the void volume were pooled separately and concentrated. The final protein concentration was assessed by OD at 280 nm using an extinction coefficient of 1.0 mg/ml-cm. Evaluation of these two pools by double diffusion and immunoelectrophoresis showed the presence of C5, C6, C7, C8, and C9 in each. Analysis by non-reduced 6.5% SDS-PAGE showed bands of $M_r$ (relative molecular weight) consistant with C5, C6, C7, and $C8^{\alpha\gamma}$ chains; $C8^\beta$ chain; C9; and S protein, with minimal contamination by other proteins. SC5b-9 from both pools was used in subsequent tests.

Purification of MC5b-9

MC5b-9 was isolated by procedure of Ware et al. *Molec. Immunol.* 18:521 (1981) modified as follows. Thirty milliliters of washed rabbit erythrocytes at $1.8 \times 10^9$ cells/ml were incubated for 10 min at 37° C. with 50% fresh human serum (to which was added a trace amount of $^{125}$I-C9) in GVBS++. Ghosts were sedimented at 31,000×g for 20 min, washed in 5 mM EDTA, resedimented, and then solubilized for 30 min in 5 mM sodium borate, 10 mM EDTA, and 1% SB-12 (Zwittergent 3-12, Calbiochem Behring Corp., La Jolla, CA) at room temperature (about 22° C. to 25° C.). The detergent-insoluble residue was removed by centrifugation, and the detergent lysate was applied to a Biogel A5M column (90×1.5 cm). The column was eluted with 5 mM sodium borate and 50 mM NaCl buffer, pH 8.8, containing 0.02% SB14 (Zwittergent 3-14, Calbiochem Behring Corp., La Jolla, CA). The trace radiolabeled C9 eluted as a single heavy molecular weight peak just behind the void volume. Nonreduced 7.5% SDS-PAGE revealed 7 bands with $M_r$ consistent with C5, C6, C7, C8 C8, C9, and C9 dimer.

Preparation of anti-C9 neoantigen

A rabbit was immunized with purified poly C9, at 50 μg per week, in complete Freund's adjuvant and bled weekly after the 4th week.

Absorption of anti-C9 neoantigen

Pooled normal human serum, purified C9, and partially purified pooled C5, C6, C7, and C8 were each linked to Sepharose 4B by the cyanogen bromide method, as outlined in the product instructions (Pharmacia Fine Chemicals, Piscataway, NJ). Antiserum to C9 neoantigen was serially absorbed against each type of immunosorbent until negligible reactivity against monomeric C9 or human plasma remained, as assessed by the ELISA described below.

Characterization of anti-C9 neoantigen

Antiserum to C9 neoantigen was initially characterized by double diffusion in 1% agarose. Further characterization of specificity was performed by ELISA. Polystyrene 96-well plates (Dynatech Immulon II, Dynatech Lab Inc., Alexandria, VA) were coated for more than 24 hr at 4° C. with 100 μl/well of either poly C9 at 0.7 μg/ml, native C9 at 0.7 μg/ml, or normal human plasma diluted 1:10, 1:100, or 1:1000 in a 0.05M sodium bicarbonate buffer, pH 9.6. The plates were washed 4 times with PBS-Tween and incubated 2 hr at room temperature with anti-C9 neoantigen diluted 1:2000 in PBS-Tween. Control wells were incubated with PBS-Tween alone at this step. The plates were washed 6 times, and all of the cells were incubated with goat anti-rabbit IgG alkaline phosphatase conjugate (Tago Inc., Burlingame, CA) at a 1:3000 dilution in PBS-Tween for 2 hr. Following this incubation, the plates were washed 6 times and developed with p-nitrophenyl phosphate (Sigma, St. Louis, MO) dissolved in 10% diethanolamine buffer, pH 9.6, at 1 mg/ml. The color reaction was stopped with 3M sodium hydroxide at 30 min, and the optical density (OD) at 405 nm was read in a MR 580 Dynatech Micro Elisa reader (Dynatech Lab Inc., Alexandria, VA). The net OD for each antigen was computed by subtracting the values of the control well from the values of the test well. Positive controls using polyclonal goat anti-C9 confirmed the binding of C9 to the plates.

Purification of IgG

Rabbit anti-C9 neoantigen IgG was purified by DEAE-Affigel Blue chromatography (BioRad, Richmond, CA), using the protocol recommended by the manufacturer.

Quantitative ELISA for SC5b-9

Figure 2:
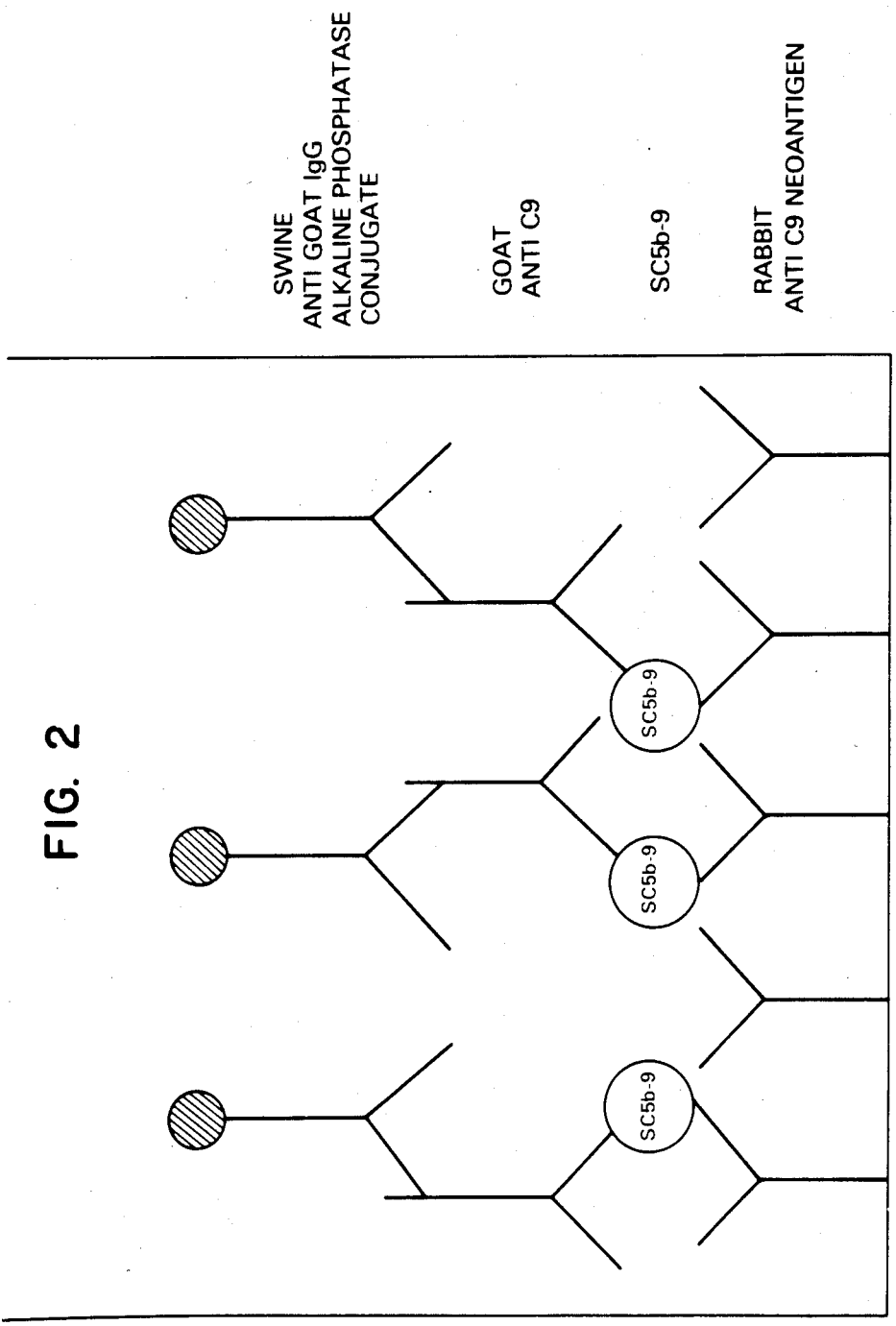
FIG. 2 shows ELISA for SC5b-9. Polystyrene plates were precoated with rabbit IgG specific for C9 neoantigen. After incubation with samples or SC5b-9 standards, the plates were developed with goat anti-C9 followed by swine anti-goat IgG alkaline phosphatase conjugate. A quantitative color reaction developed after the addition of P-nitrophenyl phosphate substrate.

Dynatech Immulon II 96-well plates were coated with 100 μl of anti-C9 neoantigen IgG at 5 μg/ml in 0.05M sodium bicarbonate buffer, pH 9.6, for more than 24 hr at 4° C. The plates were washed 4 times with PBS-Tween, and six wells for each sample were incubated for 3 hr with 100 μl each of standard dilutions of SC5b-9 in PBS tween. The plates were washed 6 times and three wells for each sample were incubated with 100 μl of goat anti-C9 (Miles Laboratories, Naperville, IL), diluted 1:2000 in PBS-Tween. At this step, three control wells for each sample were incubated with PBS-Tween alone. AFter 2 hr, the plates were washed 6 times, and all wells were incubated for an additonal 2 hr with 100 μl of swine anti-goat IgG alkaline phosphatase conjugate (Tago), diluted 1:3000 in PBS-Tween. After a final eight washes, the plates were developed with 200 μl/well of p-nitrophenyl phosphate, at 1 mg/ml, in 10% diethanolamine buffer, pH 9.6 (FIG. 2). The reaction was stopped at 45 min by adding 50 μl of 3M sodium hydroxide to each well, and OD 405 was read in a Dynatech Micro Elisa reader. The net OD for each sample was calculated by subtracting the average of triplicate control wells from the average of triplicate wells that received goat anti-native C9. A standard curve was constructed by plotting net OD vs. concentration of purified SC5b-9. The assay was also run using purified MC5b-9 and purified poly C9 as well as dilutions of normal plasma.

Characterization of anti-C9 neoantigen

By double diffusion, unabsorbed antiserum showed strong precipitin lines against poly C9 and MC5b-9. A line of partial identity was also seen with native C9 (FIG. 3). After absorption with human serum Sepharose, double diffusion revealed single precipitin lines against poly C9 and MC5b-9, but no precipitin lines against plasma or native C9. After a total of 18 immunosorbtion steps with normal serum Sepharose, C9 Sepharose, and C5, C6, C7, and C8 Sepharose, antiserum specificity was tested in a more sensitive fashion by ELISA. ELISA data supported the specificity of the antiserum for C9 neoantigen as shown in Table I indicating that antibodies to native C9 determinants as well as to other plasma proteins were removed.

TABLE I

| ANTISERUM SPECIFICITY BY ELISA | |
|---|---|
| Antigen | Net OD[a] |
| Native C9 | 0.011 |
| Poly C9 | 0.650 |
| Plasma 1:10 | 0.008 |
| Plasma 1:100 | −0.048 |
| Plasma 1:1000 | 0.001 |

[a]Mean net OD 405 from triplicate wells read at 30 min. Native C9 and poly C9 were both plated at 0.7 μg/ml. Anti-C9 neoantigen was applied to plates at 1:2000 dilution. The second antibody was a goat anti-rabbit alkaline phosphatase conjugate at a dilution of 1:3000.

Quantitative ELISA for SC5b-9

Figure 4:
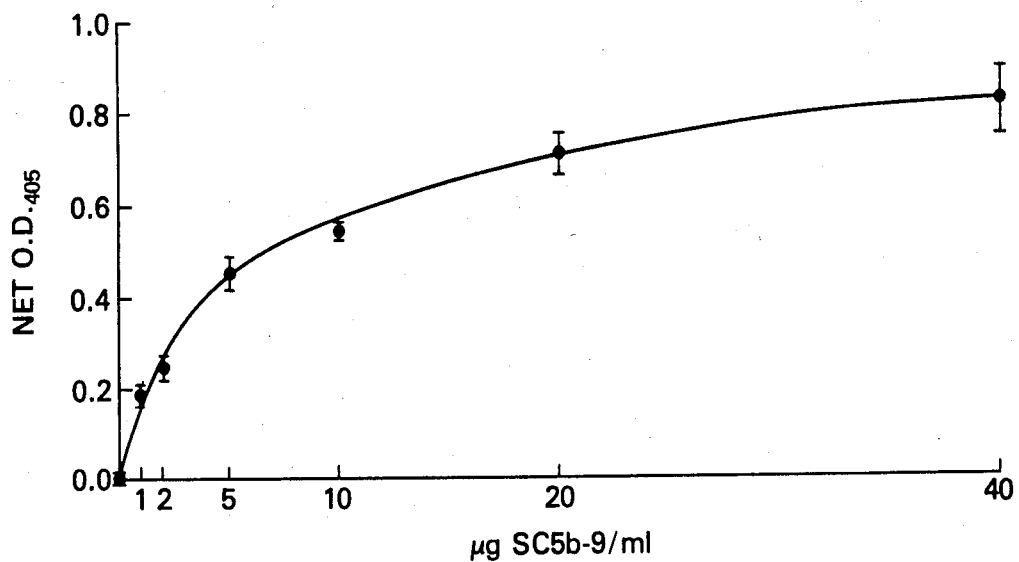
FIG. 4 shows quantitative ELISA run with dilution of purified SC5b-9. Points represent mean ±SD. A dose-response relationship with OD is demonstrated.
Figure 5:
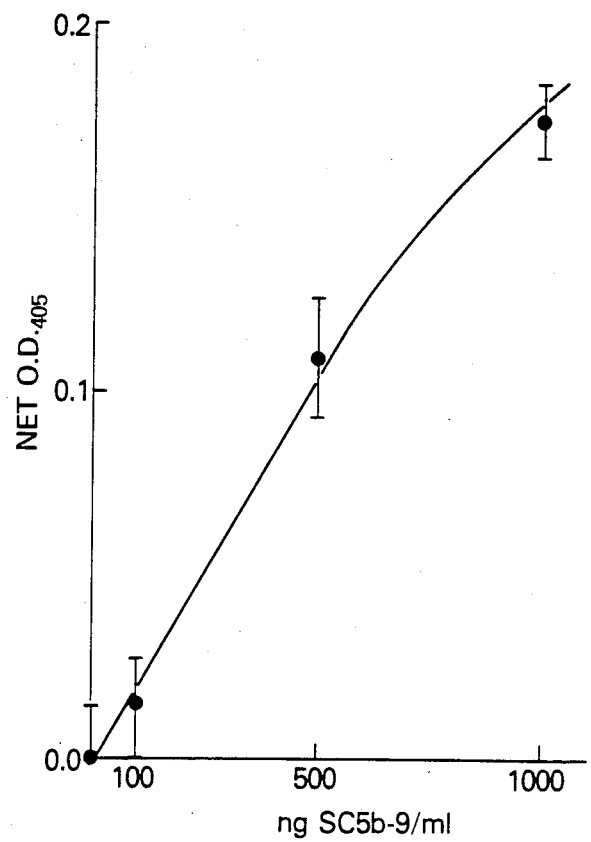
FIG. 5 shows sensitivity level of quantitative ELISA for SC5b-9. The ELISA shows a curvilinear dose response to as little as 100 ng of SC5b-9/ml.
Figure 6:
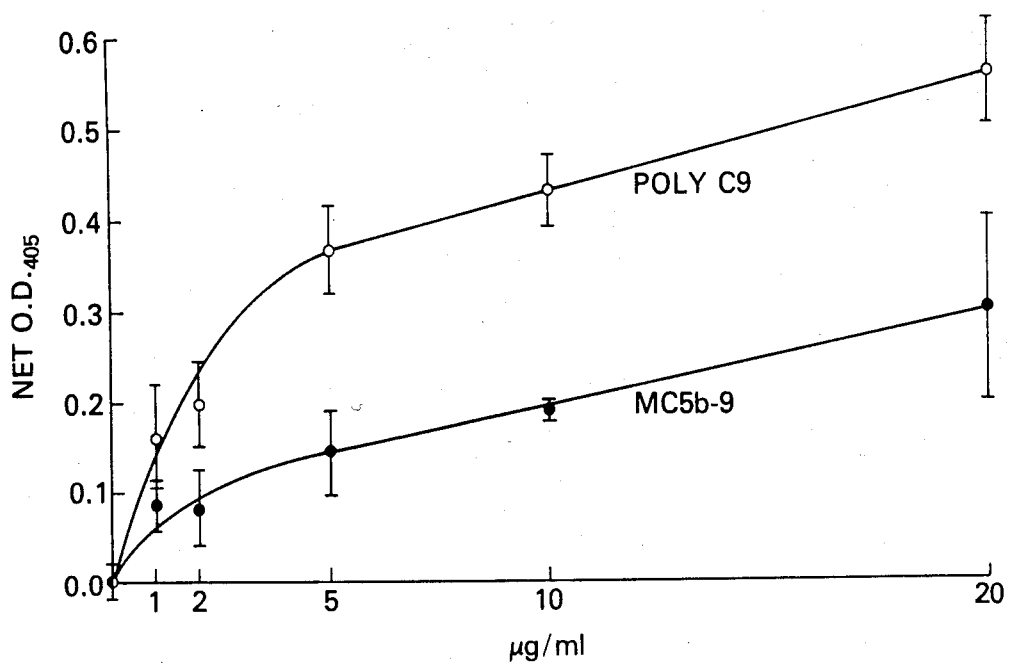
FIG. 6 shows quantitative ELISA run with dilutions of purified poly C9 and MC5b-9. Points represent mean ±SD. Dose-response relationships to OD are demonstrated for both poly C9 and MC5b-9.
Figure 7:
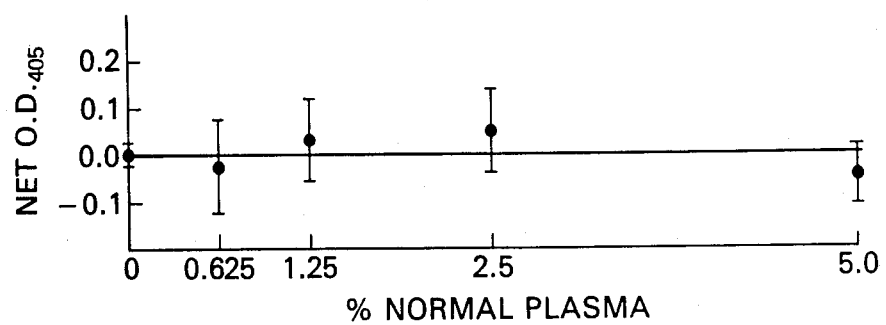
FIG. 7 shows quantitative ELISA run with dilution of normal human plasma. Points represent mean ±SD. No dose-response relationship is demonstrated.

In the quantitative ELISA, purified SC5b-9 showed a dose-response relationship with OD increasing with increasing amounts of antigen (FIG. 4). In other tests, the quantitative ELISA was shown to be sensitive to as little as 100 ng of SC5b-9/ml (FIG. 5). In order to show that the ELISA was detecting C9 neoantigen, standard curves were run with purified poly C9, MC5b-9, and dilutions of normal human plasma. As expected, both poly C9 and MC5b-9 showed dose-response relationships, with the OD increasing in response to the increasing amounts of antigen (FIG. 6). Similar curves were obtained when SC5b-9, poly C9, and MC5b-9 were diluted in 2% normal human plasma. Dilutions of normal human plasma failed to show a response in the quantitative ELISA, showing that the assay did not detect proteins present in normal plasma (FIG. 7).

The results presented above demonstrate an easily performed, sensitive ELISA which can detect and quantitate fluid phase C5b-9 complexes. In this assay, antibodies highly specific for the C9 neoantigen were used in a sandwich fashion with antibodies directed to native C9 epitopes. C5b-9 complexes in solution are bound immunologically by rabbit anti-C9 neoantigen IgG coated on a plate. Since C9 will bind to the plate only if the C9 neoantigen is expressed as in an assembled C5b-9 complex, the binding of the goat anti-native C9 can then be used to quantitate the amount of C5b-9 complexes bound on the plate, which is in turn proportional to the amount of C5b-9 complexes present in the test solution. By comparison to a standard curve generated with purified SC5b-9, the amount of SC5b-9 in an unknown sample can be assessed.

Of course, the ELISA of the present invention can be constructed using either monoclonal or polyclonal antibodies directed against any two epitopes that are found in assembled C5b-9 complexes. For instance, a monoclonal antibody to the C9 neoantigen and a biotinylated monoclonal to native C9 can be profitably employed with an avidin labelled enzyme which produces a color reaction upon addition of a suitable substrate. Alternatively anti-C5 could be used to coat the plates as a capture antibody and anti-native C9 then used as the developing antibody. A problem arises in this second alternative with the potential of the uncomplexed C5 in the sample to compete with SC5b-9 for binding to the capture antibody. This problem is avoided in the assays by the use of a capture antibody specific for a neoantigen present only in the assembled C5b-9 complex. Likewise, the enzyme employed for producing the color reaction may be preferably either alkaline-phosphatase or horseradish peroxidase or the like.

In summary, the major advantages of the present ELISA over previously published assays are that it is more sensitive, it gives a direct quantitation of SC5b-9 in nanograms per milliliter, and it can be performed without the use of radioactive materials, provided the SC5b-9 used for the standard curve is purified without the use of trace labeling. The sensitivity of the present assay, about 100 ng of SC5b-9/ml, is such that as little as a 2% activation of the terminal complement components in normal spinal fluid can be detected based on the published concentration of C9 in normal spinal fluid and the stoichiometry of SC5b-9 (Kolb and Muller-Eberhard, 1975; Morgan et al., 1984).

It should be noted that the optimal dilutions of clinical specimen in the present assay is found to be 1:50 for plasma samples and 1:2 to 1:10 for cerebrospinal fluid samples. In this range, most of the sample values fall on the steep, approximately linear portion of the curve, and interference with the assay by other proteins in the sample is minimal.

The present invention now makes it possible to use an ELISA to quantitate activation of the terminal pathway of the complement cascade. The assay measures an actual product of activation rather than consumption of components and can, therefore, be used to detect and quantitate activation of the terminal complement cascade in circumstances where normal levels of components may not be known or may be altered by other factors, such as an acute phase reactant response or a leaky blood-compartment barrier. It has been found that the present quantitative ELISA can measure SC5b-9 in the spinal fluid of patients with a variety of neurologic diseases. The sensitvity and specificity of the present assay makes it possible to monitor terminal complement activation in a variety of human diseases where such activation may be involved.

A kit in accordance with the present invention comprises containers containing a plurality of different antibodies (first, second and third antibodies as described herein), enzyme substrate, SC5b-9 standard, microtiter plate, instructions for performing the assay and the like including other accessories routinely found in similar kits.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for assaying activation of terminal complement cascade, comprising in sequence the steps of:
    (a) coating a suitable surface with a sufficient amount of a first antibody having specificity for poly C9 neoantigen;
    (b) washing said surface with a suitable medium to remove unbound antibody;
    (c) incubating said surface with a sample to be assayed for sufficient time so that binding reaction between said sample and the first antibody is substantially complete;
    (d) washing said surface with a suitable medium to remove unbound sample;
    (e) incubating said surface with a second antibody different from the first antibody and specific for a constituent of the terminal cascade for sufficient time so that binding between antigen and the second antibody is substantially complete;
    (f) thereafter washing the surface with a suitable medium to remove unbound second antibody;
    (g) incubating said surface with a third antibody which recognizes the second antibody and which is conjuncted with a suitable enzyme for a sufficient time so that the binding between said second and third antibodies is substantially complete;
    (h) washing said surface with a suitable medium to remove unbound third antibody;
    (i) incubating the surface with a substrate specific for the conjugated enzyme for sufficient time so that the enzyme-substrate reaction is substantially complete; and (j) measuring the product resulting from enzyme-substrate reaction relative to known amounts of SC5B-9 standard similarly treated as in steps (a) thru (j).

2. The method of claim 1 wherein said first, second or third antibody is monoclonal or polyclonal.

3. The method of claim 2 wherein said enzyme is alkaline phosphatase or horseradish peroxidase.

4. A method for assaying activation of terminal complement cascade, comprising in sequence the steps of:
  (a) coating a suitable surface with a sufficient amount of a first antibody having specificity for poly C9 neoantigen;
  (b) washing said surface with a suitable medium to remove unbound antibody;
  (c) incubating said surface with a sample to be assayed for sufficient time so that binding reaction between said sample and the first antibody is substantially complete;
  (d) washing said surface with a suitable medium to remove unbound sample;
  (e) incubating said surface with a second antibody different from the first antibody and specific for a constituent of the terminal cascade for sufficient time so that binding between antigen and the second antibody is substantially complete, said second antibody being conjugated with a first ligand which binds a second ligand on an enzyme applied subsequently in step (g);
  (f) thereafter washing the surface with a suitable medium to remove unbound second antibody;
  (g) incubating said surface with a ligand-conjugated enzyme which binds the ligand on the second antibody for a sufficient time so that the binding between said second antibody and enzyme is substantially complete;
  (h) washing said surface with a suitable medium to remove unbound enzyme;
  (i) incubating the surface with a substrate specific for said enzyme for sufficiet time so that the enzyme-substrate reaction is substantially complete; and
  (j) measuring the product resulting from enzyme-substrate reaction relative to known amounts of SC5b-9 standard similarly treated as in steps (a) thru (j).

5. The method of claim 4 wherein said first ligand is biotin and the second ligand is avidin.

6. The method of claim 5 wherein said enzyme is alkaline phosphatase or horse-radish peroxidase.

* * * * *